United States Patent [19]
Cooker et al.

[11] Patent Number: 5,856,534
[45] Date of Patent: Jan. 5, 1999

[54] EPOXIDATION PROCESS USING SUPPORTED SILVER CATALYSTS TREATED WITH CARBON DIOXIDE

[75] Inventors: Bernard Cooker, Malvern; Anne M. Gaffney, West Chester; Jennifer D. Jewson, Boyertown; Andrew P Kahn, Eagleville, all of Pa.

[73] Assignee: Arco Chemical Technology, L.P., Greenville, Del.

[21] Appl. No.: 993,466

[22] Filed: Dec. 18, 1997

[51] Int. Cl.$^6$ .................................................. C07D 301/10
[52] U.S. Cl. ............................................ 549/534; 549/536
[58] Field of Search ..................................... 549/534, 536

[56] References Cited

U.S. PATENT DOCUMENTS

| | | | |
|---|---|---|---|
| 1,998,878 | 4/1935 | Lefort | 260/156.5 |
| 2,615,900 | 10/1952 | Sears | 260/348.5 |
| 3,943,069 | 3/1976 | Antonelli et al. | 252/443 |
| 4,007,135 | 2/1977 | Hayden et al. | 252/467 |
| 4,066,575 | 1/1978 | Winnick | 252/475 |
| 4,212,772 | 7/1980 | Mross et al. | 252/476 |
| 4,400,308 | 8/1983 | Alter et al. | 252/463 |
| 5,625,084 | 4/1997 | Pitchai et al. | 549/536 |
| 5,698,719 | 12/1997 | Gaffney et al. | 549/534 |
| 5,703,254 | 12/1997 | Gaffney et al. | 549/536 |
| 5,770,746 | 6/1998 | Cooker et al. | 549/534 |

FOREIGN PATENT DOCUMENTS

| | | |
|---|---|---|
| 1282772 | 12/1986 | Canada . |
| 9734693 | 9/1997 | WIPO . |

*Primary Examiner*—Ba K. Trinh
*Attorney, Agent, or Firm*—Stephen D. Harper

[57] ABSTRACT

The catalytic performance of a supported silver catalyst in a propylene epoxidation process is improved by first contacting the catalyst at an elevated temperature with a treatment stream comprised of carbon dioxide. The carbon dioxide-treated catalyst is thereafter contacted with a feedstream containing propylene, molecular oxygen, but essentially no carbon dioxide under conditions effective to form propylene oxide.

20 Claims, No Drawings

EPOXIDATION PROCESS USING SUPPORTED SILVER CATALYSTS TREATED WITH CARBON DIOXIDE

FIELD OF THE INVENTION

This invention relates to a process for the direct oxidation of propylene to propylene oxide in the vapor phase using molecular oxygen in the presence of a source of chloride. In particular, the invention pertains to the use of a composition comprised of silver supported on an inert refractory solid to selectively catalyze the formation of epoxides. The performance of the catalyst is improved by exposure to a treatment stream comprised of carbon dioxide in the vapor phase. Treating the catalyst in this manner permits the epoxidation process to be operated at relatively high selectivity over an extended period of time in the substantial absence of added carbon dioxide.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier such as alpha alumina upon which the silver and promoters are deposited. A review of the direct oxidation of ethylene in the presence of supported silver catalysts is provided by Sachtler et al. in *Catalyst Reviews: Science and Engineering*, 23 (1&2), 127–149 (1981).

It is also well-known, however, that the catalysts and reaction conditions which are best suited for ethylene oxide production do not give comparable results in the direct oxidation of higher olefins such as propylene. The discovery of processes capable of providing propylene oxide by vapor phase direct oxidation in higher yields than are presently attainable thus would be most desirable.

The benefits of including carbon dioxide in the feedstream of a direct ethylene epoxidation process catalyzed by a supported silver catalyst have long been generally recognized by workers in the field. For example, Lefort, in U.S. Pat. No. 1,998,878, states that carbon dioxide may be introduced into the reactor to limit the rate of complete oxidation of ethylene to carbon dioxide. U.S. Pat. No. 2,615,900 discloses a process for producing ethylene oxide in which carbon dioxide gas is added to the feed gases to act as a "depressant" or "ant-catalytic material", thereby improving ethylene oxide selectivity. See also U.S. Pat. No. 4,007,135, which indicates that carbon dioxide may be used to raise the selectivity of the reaction.

Supported silver catalysts have traditionally been prepared by impregnating a support with a soluble silver compound and then converting the silver compound to metallic silver by "reduction" or calcining the impregnated support at an elevated temperature. U.S. Pat. No. 3,943,069 teaches such a process wherein calcination is performed in a gaseous atmosphere containing at least 1% by volume carbon dioxide. Catalysts prepared in this manner are said to have improved mechanical properties as well as high activity and selectivity in the oxidation of ethylene to ethylene oxide. Decomposition of a catalyst precursor containing a silver amine nitrate complex in an atmosphere containing carbon dioxide is suggested in U.S. Pat. No. 4,212,772. Related catalyst preparation methods employing carbon dioxide during a decomposition step are proposed in U.S. Pat. Nos. 4,066,575 and 4,400,308.

Silver catalysts supported on alkaline metal carbonates and promoted with both potassium and molybdenum compounds have been proposed for the direct conversion of propylene to propylene oxide using molecular oxygen (see U.S. Pat. No. 5,625,084). According to this patent, the inclusion of carbon dioxide in the feedstream improves propylene oxide selectivity. There is no suggestion, however, that conditioning the catalyst with carbon dioxide could lead to lasting enhancement of catalytic performance when a carbon dioxide-free feedstream is subsequently employed.

SUMMARY OF THE INVENTION

We have now unexpectedly discovered that it is possible to improve a propylene direct oxidation process using a particular type of supported catalyst containing metallic silver if the catalyst is first exposed to a vapor phase stream containing carbon dioxide at an elevated temperature. It has heretofore not been appreciated in the art that carbon dioxide treatment of such a catalyst after conversion of an impregnated silver compound to metallic silver could increase the selectivity of the catalyst for an extended period of time after carbon dioxide feed to the reactor is discontinued. That is, it has now been found that relatively short term exposure of the catalyst to carbon dioxide provides a lasting beneficial effect on catalyst selectivity which persists in the absence of the carbon dioxide. Where a tungsten promoter is incorporated into the catalyst, improvements in activity are generally also observed.

This invention thus provides a method of operating a propylene epoxidation process comprising:

(a) contacting a supported silver catalyst with a treatment stream comprised of carbon dioxide in the vapor phase at a temperature of from 150° C. to 350° C. for a time effective to improve the catalytic performance of the supported silver catalyst, wherein the supported silver catalyst is comprised of (i) an inert refractory solid support, (ii) a catalytically effective amount of metallic silver, and (iii) a promoting amount of a potassium promoter derived from a potassium salt comprising potassium cation and a nitrogen oxyanion or precursor thereof; and (b) contacting the supported silver catalyst with a feedstream comprised of propylene and molecular oxygen and essentially free of carbon dioxide in the presence of a source of chloride for a time and at a temperature effective to form propylene oxide.

DETAILED DESCRIPTION OF THE INVENTION

The present invention is directed to a process for the vapor phase oxidation of propylene to propylene oxide, i.e., an epoxidation process performed in the presence of an oxygen-containing gas and a particular class of supported silver catalysts pretreated with carbon dioxide. The process of the present invention is distinguished from the previously known olefin oxidation processes using carbon dioxide which are described in the "Background of the Invention" section of this application by the fact that the catalyst is exposed to a carbon dioxide treatment stream after conversion of a silver compound impregnated in the catalyst to metallic silver in the catalyst and before introduction of a feedstream containing propylene and molecular oxygen but essentially no carbon dioxide.

Any of the inert refractory solid materials known in the art as effective supports for silver-containing olefin oxidation catalysts may be utilized, including, for example, alumina (including alpha alumina), silicon carbide, silica, zirconia, titania, and the like. However, the support material most preferred for use in the present invention is an alkaline earth metal carbonate. Carbonates suitable for use include inorganic carbonates having a cation which is an alkaline earth metal ion, particularly calcium, strontium, magnesium or barium, with calcium carbonate being most preferred. Alkaline earth metal carbonate supports are described, for example, in Canadian Pat. No. 1,282,772.

Such support materials are capable of providing exceptionally high propylene oxide selectivities and have been found to be surprisingly superior to other support materials in this respect. The supports of the present invention may exist in various forms. In one embodiment, the support is one in which the alkaline earth metal compound is the predominant (i.e., at least 50% by weight) or, preferably, substantially the exclusive component of the support (i.e., the support consists essentially of one or more alkaline earth metal compounds). In other embodiments of the invention, the alkaline earth metal carbonate is used in conjunction with a solid substrate, i.e., a sub-support or substructure composed of a more conventional support material, such as alumina (preferably, alpha-alumina). However, the alkaline earth metal compound support material will normally comprise at least 25 weight percent (in most embodiments, at least 35 weight percent) of the finished catalyst.

The surface area of the support material generally is at least 0.6 $m^2/g$, preferably at least 1.5 $m^2/g$. However, alkaline earth metal compound support materials having relatively high surface areas (e.g., 50 to 100$m^2/g$) are also effective for the purposes of this invention. This result was surprising in view of the preference generally expressed in the direct olefin oxidation field for low surface area supports (typically, 0.03 to 10 $m^2/g$). The surface area is measured by the conventional B. E. T. method using nitrogen or krypton described by Brunauer, Emmett and Teller in *J. Am. Chem. Soc.* 60, 309–16 (1938).

The support materials used in the present invention may generally be described as porous or microporous and typically have water pore volumes of about 0.05 to 0.80 cc/g.

The supported catalyst used in the present invention may be prepared by any known method of introducing silver and/or a promoter in soluble form to a support. Suitable methods are described, for example, in Canadian Patent No.1,282,772 and U.S. Pat. No. 5,625,084, which are incorporated herein by reference in their entirety. A preferred method of introducing silver to the support is by an impregnation process in which a solution of a silver compound (which can be a salt or complex of silver) in an amount sufficient to deposit the desired weight of silver upon the support is dissolved in a suitable solvent or "complexing/solubilizing" agent. The solution may be used to impregnate the support by immersing the support in the silver compound-containing impregnating solution and forming a pasty mixture or slurry. The slurry is then dried and calcined by placing the mixture in an oven or furnace at about 100° to about 120° C. for 0.5 to 6 hours and then heating the mixture at a temperature of from about 250° to about 600° C. for another 1 to 6 hours. This procedure accomplishes drying of the support/silver mixture, removes volatile components and reduces the silver present to its elemental form.

The potassium salt and optional metal promoter compound(s) may be introduced to the catalyst, either simultaneously or separately, as impregnation solutions in a separate impregnation step or steps. Again, this may be done by any known manner of impregnating a porous material. Conveniently, this may be carried out by placing the catalyst material in a container, evacuating the container and thereafter introducing the solution(s). Alternatively, the support may be sprayed or sprinkled with the impregnating solution (s). The excess solution may then be allowed to drain off or the solvent may be removed by evaporation under reduced pressure at a suitable temperature. The catalyst may then be dried at a moderate temperature (e.g., at 120° C.) in a oven (one-half to five hours typically being sufficient). Such a procedure is known as a "sequential" or "consecutive" method of preparation. The supported catalyst may also be prepared by a "simultaneous" or "coincidental" method of preparation. With this method, the potassium salt and the optional metal promoter compound(s) are included in the silver compound-containing solution used to impregnate the support. In yet another embodiment, the support is impregnated with the silver compound (optionally, also with one or more metal promoter compounds), calcined, impregnated with the potassium salt, and then dried without calcination.

The choice of silver compound used to form the silver-containing impregnating solution in a solvent or a complexing/solubilizing agent is not particularly critical and any silver compound generally known to the art which is both soluble in and does not react with the solvent or complexing/solubilizing agent to form an unwanted product and which is capable of being converted to metallic silver may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, fatty acid ester, and the like or combinations thereof. In one embodiment, silver (I) oxide is utilized.

A large number of solvents or complexing/solubilizing agents may be suitably used to form the silver compound-containing impregnating solution. Besides adequately dissolving the silver compound or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide silver in the finished catalyst to the extent of preferably about 2 to about 70 percent silver, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the silver compound-containing solution are alcohols, including glycols, such as ethylene glycol, amines (including alkanolamines such as ethanolamine and alkyldiamines such as ethylene-diamine) and carboxylic acids, such as lactic acid and oxalic acid, as well as aqueous mixtures of such materials.

Typically, a silver compound-containing solution is prepared by dissolving a silver compound in a suitable solvent or complexing/solubilizing agent such as, for example, a mixture of water, ethylenediamine, oxalic acid, silver oxide, and monoethanolamine. The solution is then mixed with support particles and drained. Thereafter the particles are suitably dried.

As indicated above, after impregnation, the silver compound-impregnated support particles are treated to convert the silver compound to silver metal and thereby effect deposition of silver on the surface of the support. As used herein, the term "surface", as applied to the support, includes not only the external surfaces of the support but also the internal surfaces, that is, the surfaces defining the pores or internal portion of the support particles. This may be done by treating the impregnated particles with a reducing agent, such as hydrogen or hydrazine and/or by roasting (calcining), at an elevated temperature to decompose the silver compound and reduce the silver to its free metallic state. Certain solubilizing agents such as alkanolamines, alkyldiamines, and the like may also function as reducing agents.

Although at least a catalytically effective amount of metallic silver must be present in the finished catalyst (meaning an amount that provides a measurable conversion of propylene to propylene oxide), the metallic silver concentration preferably is from about 2 percent to 70 percent, by weight, based on the total weight of the catalyst. More preferably, the metallic silver concentration ranges from about 10 to 60 percent by weight.

It has been unexpectedly discovered that the presence of potassium in the supported silver catalyst significantly enhances the efficiency of said catalyst as a propylene epoxidation catalyst. Surprisingly, other alkali metals such as cesium which are well-known as promoters in the ethylene oxide art fail to improve catalyst performance to an appreciable extent. The potassium is introduced by means of a potassium salt, with the selection of particular anions as counter ions to the potassium cation being found to be critical to the attainment of optimum catalyst performance. The anion must be a nitrogen oxyanion (i.e., an anion or negative ion which contains both nitrogen and oxygen atoms such as nitrate or nitrite) or a precursor thereof. Potassium compounds containing species capable of being converted to nitrogen oxyanions under the catalyst preparation or epoxidation conditions (i.e., which are nitrogen oxyanion precursors) are thus also suitable for use. Carbon oxyanions such as carbonate and bicarbonate, for example, may be employed. Conversion of such carbon oxyanions to nitrogen oxyanions may be accomplished, for example, by treating the catalyst with a stream comprised of a gaseous nitrogen oxide species such as NO at an elevated temperature (e.g., 180° C. to 320° C.).

The efficiency-enhancing potassium salt may be introduced to the catalyst in any known manner. Thus, impregnation and deposition of silver and the potassium salt may be effected coincidentally or sequentially. For example, the support could be impregnated with a solution or solutions of the potassium salt and silver compound, dried, and then calcined to reduce the silver compound and generate the active supported silver catalyst. Alternatively, the support may be impregnated with the silver compound, dried, calcined, and then re-impregnated with the potassium salt.

In order to perform coincidental impregnation, the potassium salt must be soluble in the same solvent or complexing/solubilizing agent used with the silver impregnating solution. With a sequential procedure in which the silver is added first, any solvent capable of dissolving the salt which will neither react with the silver nor leach it from the support is suitable. Aqueous solutions are generally preferred, but organic liquids, such as alcohols, may also be employed. Suitable procedures for effecting introduction of a potassium salt to a solid support are well known in the art.

The potassium salt is used in an amount sufficient to provide a potassium promoter concentration which results in an improvement in one or more of the catalytic properties (e.g., selectivity, activity, conversion, stability, yield) of the supported silver catalyst as compared to a catalyst not containing the potassium promoter. The precise amount will vary depending upon such variables as the composition in the feed stream, the amount of silver contained in the catalyst, the surface area of the support, the process conditions, e.g., space velocity and temperature, and morphology of support. It has been found, however, that a minimum of at least 0.5 percent by weight of the potassium promoter, calculated as cation, based on the total weight of the catalyst must be present for the catalyst to exhibit a significant advantage over an analogous catalyst containing no potassium promoter. Potassium concentrations as high as 10 percent by weight may be utilized, although generally little additional benefit is realized beyond a concentration of 5 weight percent. More preferably, the potassium promoter level is an amount corresponding to about 1 to about 3 weight percent K.

An optional component of the supported silver catalysts used in this invention is a promoting amount of one or more metal promoters. Preferred metal promoters include Re, Mo, W and the like, either alone or in combination with other metal promoters. Catalysts containing such promoters tend to exhibit greater improvement in performance when treated with carbon dioxide in accordance with this invention than do analogous catalysts lacking such promoters. "Promoting amount" means an amount that works effectively to provide an improvement in one or more catalytic properties of a catalyst as compared to a catalyst not containing a metal promoter. The exact form of the metal promoters under epoxidation operating conditions is not known. The metal promoters, it is believed, are not present on the catalyst in the elemental form since the promoters are applied to the catalyst in the form of compounds (including ions, salts and/or complexes) and the reducing conditions generally used to reduce the silver to metallic silver are not usually sufficient to reduce the metal promoter compounds to the elemental form.

It is thought that the metal promoters deposited on the support or present on the catalyst are in the compound form, most probably in the form of oxygen-containing or oxidic compounds. In a presently preferred embodiment, the metal promoters are introduced to the catalyst in the oxyanionic form, i.e., in the form of anions, or negative ions which contain oxygen. Examples of anions of metals that can be suitably applied include the molybdates, tungstates and perrhenates. The anions can be prepared by the reactive dissolution of various non-anionic metal compounds such as the oxides (e.g., $MoO_3$, $WO_3$, $Re_2O_7$) as well as other materials such as acids, carbonates, sulfates, halides, oxyhalides, hydroxyhalides, hydroxides, sulfides, etc., of the metal. The cation forming the counter ion to the anion in the metal promoter compound is most suitably ammonium, although alkali metal or alkaline earth metal cations may also be utilized. In the embodiment of the invention where the chloride source is supplied by incorporating an inorganic chloride compound into the catalyst, the chlorides of Mo, Re and W may advantageously be used.

The support is optionally impregnated with one or more metal promoter compounds. This may be done at the same time that the other components of the catalyst are added or before and/or later. In one advantageous and convenient embodiment of the invention, the optional metal promoter compound(s), potassium salt and silver are incorporated into the catalyst simultaneously. In another embodiment, however, the potassium salt is introduced by impregnation after the silver compound is converted to metallic silver.

While not critical, it has generally been found that the minimum amount of metal promoter present in or deposited on the support or catalyst needed to measurably improve catalyst performance is approximately 0.1 weight percent metal (measured as the element irrespective of the form in which the promoter is present) based on the total weight of the supported silver catalyst where the metal is selected from the group consisting of W, Mo, Re and combinations thereof. Generally speaking, the maximum amount of metal promoter will be 10 weight percent. Operation within the range of 0.2 to 2.5 weight of metal promoter is particularly advantageous.

The degree of benefit obtained within the above-defined limits will vary depending upon particular properties and characteristics, such as, for example, reaction conditions, catalyst preparative techniques, surface area and pore structure and surface chemical properties of the support utilized, silver content of the catalyst, and potassium content of the catalyst.

The presence of the indicated and claimed amounts of optional metal promoters in this specification and claims does not preclude the use of other activators, promoters, enhancers, stabilizers, improvers, and the like.

The metal promoter compounds optionally used in the preparation of the instant catalysts can be compounds that can be solubilized in an appropriate solvent. Preferably, the solvent is a water-containing solvent. More preferably the solvent is the same solvent used to deposit the silver compound and potassium salt. Alternatively, generally insoluble metal promoter compounds such as $MoCl_5$ can be employed.

It is essential that the supported silver catalyst prepared as previously described herein be pretreated by exposure to a gaseous stream comprised of carbon dioxide at a temperature of at least 150° C. (preferably, at least 200° C.) but no greater than 350° C. (preferably, no greater than 300° C.). The pretreatment step of the method claimed herein may conveniently be performed in the same apparatus or reactor in which the epoxidation step is carried out, for example, as part of the start-up of a propylene oxide plant or, if so desired, in a different vessel of suitable configuration. It will generally be advantageous to deploy the untreated catalyst in the form of a fixed bed and to pass the gaseous stream containing carbon dioxide through the fixed catalyst bed in a substantially continuous manner. Gas hourly space velocities of from about 100 to 10,000 $hr^{-1}$ are typically preferred. Such contacting is continued for a time sufficient to improve the catalytic performance of the catalyst as compared to the untreated catalyst. Without wishing to be bound by theory, it is believed that treatment with carbon dioxide converts a portion of the metallic silver in the catalyst to silver carbonate and that silver carbonate is a precursor to an active silver species which participates in the desired epoxidation reaction.

The concentration of carbon dioxide in the treatment stream should be higher than what is normally present in air (ca. 300 ppm) with concentrations of at least 1 vol. % being preferred. In one desirable embodiment, a treatment stream comprising at least 5 vol. % $CO_2$ is utilized. Higher concentrations of carbon dioxide in the treatment stream are also suitable for use. For example, the carbon dioxide may be 50 vol. % or higher (e.g., up to 100% carbon dioxide). The treatment time generally will range from about 1 to 100 hours. The pretreatment step may be performed at relatively low or relatively high pressures, with the range of from about 15 to 500 psig generally being suitable. The optimum treatment time and pressure will be influenced by other reaction variables such as temperature and carbon dioxide concentration as well as the composition of the catalyst, but may be readily determined by experimentation.

In some circumstances, it has been found that the inclusion of molecular oxygen in the treatment stream will further improve the performance of the catalyst. The treatment stream thus may be suitably comprised of at least 1 volume % $O_2$. Exceptionally high levels of molecular oxygen in the treatment stream will generally be undesirable for safety or economic reasons. Typically, no more than about 10 vol. % $O_2$ is utilized. The balance of the treatment stream may be an inert gas such as nitrogen or the like, although hydrocarbons such as propylene, methane, and the like could also be present. In one embodiment of the invention, however, a treatment stream is used which is essentially free of propylene or other reactive olefins. If propylene and other reactive olefins are omitted, it may be advantageous to include water in the treatment stream. Thus, in this embodiment, the treatment stream may consist essentially of carbon dioxide, an inert ballast gas, and, optionally, molecular oxygen and/or water. In another embodiment, the treatment stream contains propylene (e.g., up to 50 volume %) in addition to carbon dioxide and molecular oxygen such that epoxidation is carried out simultaneously with catalyst conditioning.

The supported silver catalyst may additionally be treated with other substances in addition to carbon dioxide, either prior to, during, or subsequent to the carbon dioxide pretreatment step in order to further improve or optimize its catalytic properties. For example, the catalyst may be contacted with water (either as such or in the form of a compound capable of generating water under the treatment conditions) and/or an organic chloride and/or a nitrogen oxide species. Examples of nitrogen oxide species suitable for use include NO, $NO_2$, $N_2O_4$, $N_2O_3$ or mixtures thereof, with NO being the most preferred nitrogen oxide species. Typically, the concentration of the nitrogen oxide species in the gaseous stream used to treat the supported silver catalyst will be in the range of about 10 to 2000 ppm. Temperatures of from 150° C. to 350° C. are usually sufficient for this purpose.

To achieve optimum catalyst productivity, it is highly desirable to operate the epoxidation process of this invention such that a source of chloride is present while the carbon dioxide-pretreated supported silver catalyst is being contacted with the feedstream.

In one embodiment of the invention, the chloride source is supplied by including a chloride compound in the feedstream. Preferably, the chloride compound is organic in character. More preferably, the organic chloride is selected from those organic compounds containing from 1 to 10 carbon atoms (more preferably, 1 to 4 carbon atoms) and at least one chlorine atom. Other elements such as hydrogen, oxygen, nitrogen, sulfur, and halogens other than chlorine may also be present, but preferably the organic chloride consists only of hydrogen, carbon and chlorine atoms or only of carbon and chlorine atoms. Saturated organic chlorides are generally preferred for use. Illustrative organic chlorides include, but are not limited to, methyl chloride, ethyl chloride (an especially preferred organic chloride), propyl chloride, butyl chloride, methylene chloride, chloroform, carbon tetrachloride, ethylene dichloride, vinyl chloride, chloro cyclohexane, chlorobenzene, and the like. Suitable concentrations of chloride compound in the feedstream include the range of from 1 to 2000 ppm.

In another embodiment, the supported silver catalyst is pretreated with a chloride compound (preferably selected from among the compounds described in the preceding paragraph) and oxygen in the gas phase at an elevated temperature (e.g., 180° C. to 320° C.) prior to epoxidation, as described in U.S. application Ser. No. 08/880,896, filed Jun. 23, 1997 (Attorney's Docket No. 01-2442A) which is incorporated herein by reference in its entirety. Catalysts pretreated in this manner contain chloride, presumably in the form of an inorganic chloride compound such as silver chloride, which helps to improve catalyst performance during epoxidation. Alternatively, an inorganic chloride compound such as silver chloride or other transition metal chloride is incorporated directly into the catalyst during preparation, as described in U.S. application Ser. No. 08/880905, filed Jun. 23, 1997 (Attorney's Docket No.01-2454A), incorporated herein by reference in its entirety. In the latter two embodiments of the invention, it is desirable for the catalyst to contain from 0.1 to 2 weight percent Cl. Different sources of chloride may, of course, be utilized simultaneously.

In a subsequent step of this invention, a feedstream comprising propylene and molecular oxygen (but essentially no carbon dioxide) is contacted with the previously described carbon dioxide-treated catalyst in a reactor under conditions effective to accomplish at least partial oxidation of the propylene to the corresponding epoxide. Typical epoxidation conditions include temperatures within the reaction zone of the reactor on the order of about 180° to 350° C. (more preferably, 200° to 300° C.) and pressures from about 1 to about 60 atmospheres. The feedstream is essentially free of carbon dioxide. "Essentially free" in this context means that no carbon dioxide is added to the feedstream beyond what may be inherently present as an impurity in the molecular oxygen source, propylene, or inert ballast gas used in the process (typically, no more than 500 ppm). Some carbon dioxide may, of course, be formed during epoxidation and thus be present in the reactor as a result of overoxidation of the propylene.

A gaseous nitrogen oxide species may also be supplied to the reaction zone within the reactor by introducing said species to the feedstream containing propylene (fresh and/or recycled) and molecular oxygen. The introduction of gaseous nitrogen oxide species, while not mandatory, is extremely beneficial to epoxidation performance as it helps to promote a relatively high level of catalytic activity without sacrificing propylene oxide selectivity. The optimum amount is determined, in part, by the particular potassium salt and metal promoter compound (if any) used and the concentrations thereof, and by other factors noted above which influence the optimum amount of potassium salt and metal promoter. Typically, a suitable concentration of the nitrogen oxide species for epoxidation of propylene is about 0.1 to about 2,000 ppm by volume.

The "oxygen" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. The oxygen is typically introduced to the reactor either as air, commercially pure oxygen or other substance which under epoxidation conditions both exists in a gaseous state and forms molecular oxygen. The concentration of oxygen in the feedstream may suitably be from about 2 to 15 vol. %.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feedstream having the particular composition previously described thus may be formed prior to or at the time the individual components thereof enter the reaction zone. The feedstream may utilize or incorporate a recycle stream from the reactor. The use of the term "feedstream" herein thus is not meant to limit the present process to the embodiment where all of the gaseous components are combined prior to introduction of said components into the reaction zone. The reactors in which the process and catalyst of the present invention are employed may be of any type known to the art.

The feedstream may also contain a ballast or diluent, such as nitrogen or other inert gas, particularly when air is used as the source of oxygen. Varying amounts of water vapor may also be present.

The components of the feedstream are most suitably present in the amounts shown in the following table:

| Component | Volume in % (or ppm) for Propylene Oxidation |
| --- | --- |
| propylene | about 2 to about 50% |
| oxygen | about 2 to about 15% |
| organic chloride | 0–2,000 ppm, preferably at least 1 ppm if no other source of chloride is present |
| nitrogen oxide species | 0–2,000 ppm, |
| carbon dioxide | not more than 500 ppm |
| nitrogen or other ballast gas | remainder. |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxide reactors. These generally include wall-cooled as well as adiabatic or non-wall-cooled reactors. The conditioning and epoxidation steps may be conveniently carried out in the same reactor, as there will generally be no need to use different equipment for each step. This will minimize the amount of time required to start up and operate an epoxidation unit. Tube lengths may typically range from about 5 to about 60 feet but will frequently be in the range of from about 15 to about 45 feet. The tubes may have internal diameters from about 0.5 to about 2.5 inches and are expected to be typically from about 0.8 to about 1.5 inches. A plurality of tubes packed with catalyst arranged in parallel within a suitable shell may be employed. GHSV generally ranges from about 500 to about 10,000 hr$^{-1}$. Typically, GHSV values range from about 200 to about 3,000 hour$^{-1}$ at pressures from about 1 to about 60 atmospheres, commonly about 1.1 to about 30 atmospheres. Contact times should be sufficient to convert 0.5 to 70%, preferably 5 to 30%, of the propylene.

While the benefits provided by carbon dioxide treatment of the catalyst are remarkably persistent, it may be desirable to periodically regenerate or reactivate the catalyst by recontacting the used catalyst with carbon dioxide for a suitable period of time under the conditions described previously for the initial treatment step. Carbon dioxide feed is discontinued once catalyst performance has been restored to the desired extent.

EXAMPLES

Example 1

This example demonstrates the process of the invention using a tungsten/potassium nitrate-promoted silver catalyst supported on calcium carbonate.

To prepare the catalyst, the following materials were combined in a 16 oz. jar containing 5 ceramic stones: ethylene diamine (20.7 g), distilled water (20.4 g), oxalic acid dihydrate (15.0 g), silver (I) oxide (26.0 g), ethanolamine (7.2 g), a solution of potassium tungstate (5.32 g) in distilled water (5.0 g), and calcium carbonate (34.0 g). The jar was sealed and placed on a ball mill for 4 hours. The mixture was then dried at 110° C. for 1 hour and calcined at 300° C. for 3 hours. Elemental analysis indicated that the supported silver catalyst contained 40 wt. % Ag, 2 wt. % K and 4.7 wt. % W. The catalyst was pressed and sieved to 14/30 mesh prior to use in epoxidation.

The freshly prepared catalyst was evaluated in propylene epoxidation using a feedstream containing 10 vol. % propylene, 5 vol. % $O_2$, 200 ppm NO and 50 ppm ethyl chloride (balance $N_2$; 1200 $hr^{-1}$ GHSV). After 41.7 hours at 258° C. and 40 psig, propylene oxide selectivity was 36%, propylene conversion 12%, and propylene oxide productivity was 0.87 $lb/ft^3 \cdot hr$.

The amount of carbon dioxide in the feedstream was thereafter increased, then reduced again to zero as shown in the following table; all other reaction conditions remained unchanged.

| Time at Condition hrs | $CO_2$, vol. % | PO Selectivity % | Propylene Conversion. % | PO Productivity $lb/ft^3 \cdot hr$ |
| --- | --- | --- | --- | --- |
| 25.0 | 5 | 44 | 13 | 1.06 |
| 18.3 | 10 | 48 | 12 | 1.04 |
| 66.7 | 25 | 54 | 10 | 0.88 |
| 21.7 | 50 | 56 | 7 | 0.77 |
| 20.0 | 0 | 41 | 13 | 0.97 |

Comparison of the results obtained after eliminating carbon dioxide from the feedstream with those obtained initially in the absence of carbon dioxide confirms that a 5 point improvement in propylene oxide selectivity and a 14% increase in PO productivity was achieved by treating the supported silver catalyst with carbon dioxide. It has not previously been appreciated in the prior art that carbon dioxide treatment of such a catalyst would provide a persistent beneficial effect when carbon dioxide feed is discontinued.

Example 2

A potassium nitrate-promoted silver catalyst supported on calcium carbonate was prepared as described in accordance with the procedures described in U.S. Pat. No. 5,625,084 (omitting Mo promoter), with the catalyst being simultaneously impregnated with the potassium salt and the silver compound. The elemental composition of the catalyst was approximately as follows: 40 wt. % Ag, 2 wt. % K. The performance of the catalyst was evaluated under the following process conditions: 10 vol. % propylene, 5 vol. % oxygen, 50 ppm ethyl chloride, 200 ppm NO, 260° C., 40 psig, 1200 $hr^-$ GHSV, 2 cc catalyst. The catalyst was initially evaluated for approximately 1 day using a feedstream of the aforementioned composition containing no carbon dioxide. Thereafter, the amount of $CO_2$ in the treatment stream was gradually increased to 50 vol. % (approximately 3 days at 5 vol. % $CO_2$, 1 day each at 10 and 25 vol. % $CO_2$). After 1 day at 50 vol. % $CO_2$, the initial feedstream composition (0 vol. % $CO_2$) was restored. The reaction temperature was lowered somewhat before returning to the initial conditions. Both propylene oxide selectivity and productivity improved as compared to the initial evaluation performance, with propylene conversion dropping slightly.

| | PO Selectivity % | Propylene Conversion. % | PO Productivity $lb/ft^3 \cdot hr$ |
| --- | --- | --- | --- |
| Before $CO_2$ Treatment | 32 | 12.6 | 0.75 |
| After $CO_2$ Treatment | 35 | 12.4 | 0.80 |

Example 3

Example 2 was repeated, except that the reaction temperature was not lowered prior to returning to the initial conditions and the increase in $CO_2$ content of the treatment stream was controlled as follows: ca. 2 days at 0 vol. % $CO_2$, 1 day each at 5 and 10 vol. % $CO_2$, 3 days at 25 vol. % $CO_2$, and 1 day at 50 vol. % $CO_2$. Under these particular conditions, minimal changes in catalyst performance were observed.

| | PO Selectivity % | Propylene Conversion. % | PO Productivity $lb/ft^3 \cdot hr$ |
| --- | --- | --- | --- |
| Before $CO_2$ Treatment | 34 | 13 | 0.84 |
| After $CO_2$ Treatment | 35 | 13 | 0.81 |

Example 4

Example 3 was repeated, but using a molybdenum-promoted silver catalyst supported on calcium carbonate prepared as described in U.S. Pat. No. 5,625,084 (50 wt. % Ag, 0.5 wt. % Mo, 2 wt. % K, added sequentially after calcination). After treatment with carbon dioxide (ca. 4 days at 0 vol. % $CO_2$, 1 day each at 5, 10, 25 and 50 vol. % $CO_2$), the catalytic performance as measured by PO selectivity and productivity was significantly enhanced. No loss of activity was observed.

| | PO Selectivity % | Propylene Conversion. % | PO Productivity $lb/ft^3 \cdot hr$ |
| --- | --- | --- | --- |
| Before $CO_2$ Treatment | 42 | 13.0 | 0.95 |
| After $CO_2$ Treatment | 44 | 13.0 | 1.03 |

Example 5

Example 3 was repeated, but using a tungsten-promoted silver catalyst supported on calcium carbonate prepared by co-impregnation of $KNO_3$ and $(NH_4)_{10} W_{12}O_{41} \cdot 5H_2O$. The catalyst contained 40 wt. % Ag, 0.5 wt. % W and 2 wt. % K. After treatment with 50 vol. % $CO_2$ at 250° C. for approximately 1 day, the productivity of the catalyst was improved.

| | PO Selectivity % | Propylene Conversion. % | PO Productivity $lb/ft^3 \cdot hr$ |
| --- | --- | --- | --- |
| Before $CO_2$ Treatment | 37 | 11 | 0.85 |
| After $CO_2$ Treatment | 37 | 12 | 0.89 |

We claim:

1. A method of operating a propylene epoxidation process comprising:

(a) contacting a supported silver catalyst with a treatment stream comprised of carbon dioxide in the vapor phase at a temperature of from 150° C. to 350° C. for a time effective to improve the catalytic performance of the supported silver catalyst, wherein the supported silver catalyst is comprised of (i) an inert refractory solid support, (ii) a catalytically effective amount of metallic silver, and (iii) a promoting amount of a potassium promoter derived from a potassium salt comprising potassium cation and a nitrogen oxyanion or precursor thereof; and (b) contacting the supported silver catalyst with a feedstream comprised of propylene and molecular oxygen and essentially free of carbon dioxide in the presence of a source of chloride for a time and at a temperature effective to form propylene oxide.

2. The method of claim 1 wherein the inert refractory solid support is comprised of an alkaline earth metal carbonate.

3. The method of claim 1 wherein the treatment stream is comprised of at least 5 volume percent carbon dioxide.

4. The method of claim 1 wherein the supported silver catalyst is additionally comprised of a promoting amount of a metal selected from the group consisting of molybdenum, rhenium, tungsten and mixtures thereof.

5. The method of claim 1 wherein the treatment stream is essentially free of propylene.

6. The method of claim 1 wherein the feedstream is additionally comprised of a nitrogen oxide species.

7. The method of claim 1 wherein the source of chloride is a $C_1$–$C_{10}$ organic chloride incorporated in the feedstream.

8. The method of claim 1 wherein the treatment stream additionally comprises a compound selected from molecular oxygen, propylene, water, or mixtures thereof.

9. The method of claim 1 wherein the potassium salt is selected from the group consisting of potassium carbonate, potassium bicarbonate, potassium nitrate, potassium nitrite, and mixtures thereof.

10. The method of claim 1 wherein the source of chloride is an inorganic chloride compound incorporated in the supported silver catalyst.

11. A method of operating a propylene epoxidation process comprising:

(a) contacting a supported silver catalyst with a treatment stream comprised of at least 5 volume percent carbon dioxide in the vapor phase at a temperature of from 200° C. to 300° C. for a time effective to improve the catalytic performance of the supported silver catalyst, wherein the supported silver catalyst is comprised of (i) an inert refractory support comprised of an alkaline earth metal carbonate, (ii) from 10 to 60 weight percent metallic silver, and (iii) a promoting amount of a potassium promoter derived from a potassium salt selected from the group consisting of potassium nitrate, potassium nitrite, potassium carbonate, potassium bicarbonate and mixtures thereof; and (b) contacting the supported silver catalyst with a feedstream comprised of propylene and molecular oxygen and essentially free of carbon dioxide in the presence of a source of chloride selected from the group consisting of $C_1$–$C_{10}$ organic chloride compounds, inorganic chloride compounds, and combinations thereof at a temperature of from 200° C. to 300° C. for a time effective to form propylene oxide.

12. The method of claim 11 wherein the treatment stream is essentially free of propylene.

13. The method of claim 11 wherein the supported silver catalyst is additionally comprised of from 0.2 to 2.5 weight percent of a metal promoter selected from the group consisting of molybdenum, rhenium, tungsten and mixtures thereof.

14. The method of claim 11 wherein the treatment stream additionally comprises a compound selected from molecular oxygen, propylene, water, or mixtures thereof.

15. The method of claim 11 wherein the feedstream is additionally comprised of from 1 to 2000 ppm of a $C_1$–$C_4$ organic chloride.

16. The method of claim 11 wherein the supported silver catalyst is additionally comprised of an inorganic chloride compound.

17. The method of claim 11 wherein the alkaline earth metal carbonate is calcium carbonate.

18. The method of claim 11 wherein the feedstream is additionally comprised of from 0.1 to 2000 ppm of a nitrogen oxide species.

19. The method of claim 11 wherein said step (a) is repeated periodically.

20. The method of claim 11 wherein the supported silver catalyst is obtained by a procedure comprising the steps of impregnating the inert refractory support with a silver compound and converting the silver compound to metallic silver.

* * * * *